Feb. 24, 1948. T. J. MORRIS Plant Pat. 785
ROSE PLANT
Filed Nov. 4, 1946
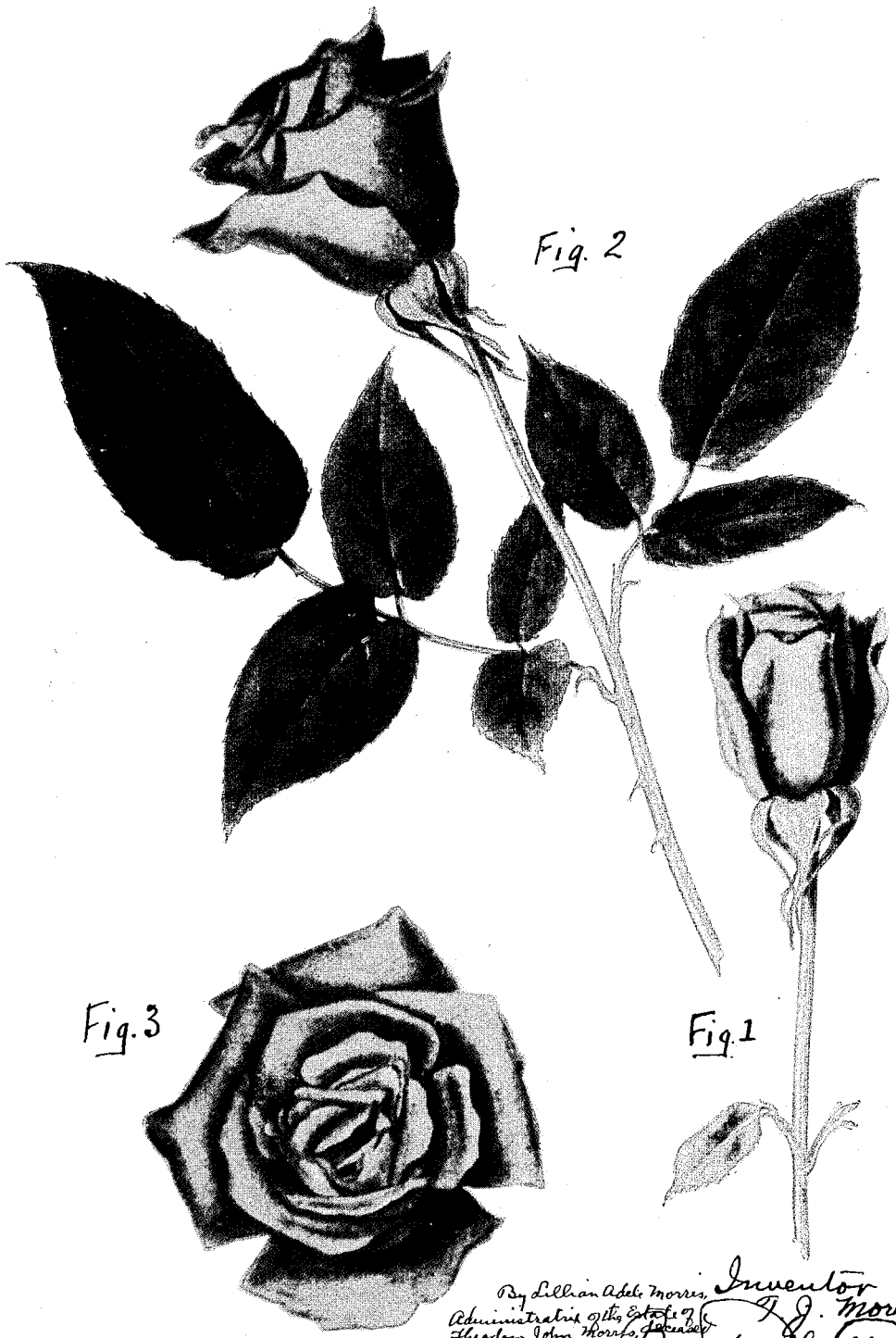
By Lillian Adele Morris, Administratrix of the Estate of Theodore John Morris, Deceased
Inventor
T. J. Morris
By Robert Robb
Attorneys.

Patented Feb. 24, 1948 Plant Pat. 785

UNITED STATES PATENT OFFICE

785

ROSE PLANT

Theodore John Morris, deceased, late of Van Nuys, Calif., by Lillian Adele Morris, administratrix, Van Nuys, Calif., assignor to Western Rose Co., Van Nuys, Calif., a copartnership composed of Albert B. Morris and Lillian Adele Morris Application November 4, 1946, Serial No. 707,649

1 Claim. (Cl. 47—61)

The present invention relates to a new and distinct variety of rose plant, particularly adapted for cut-flower production, whether grown outdoors or in a greenhouse.

The outstanding characteristics of this variety, which serve cut-flower purposes especially, are its profuse blooming habit, continuity of such blooming throughout the blooming season, even in hot weather, the distinctively attractive color of the flowers, and the retention of their form and color until they fall. It is to be understood, however, that the field of utility of this new rose is not restricted to that of cut-flowers, since its floriferousness and long lasting color make this variety equally desirable for garden display.

In the drawing:

Fig. 1 shows a specimen of bud before the petals unfurl:

Fig. 2 shows a specimen of foliage and bloom at about half-blown stage; and

Fig. 3 is a top plan of a bloom at full-blown stage.

Asexual reproduction of this new rose variety shows the foregoing characteristics come true to form and are established.

The following is a detail description of this new variety, color terminology, where indicated by chart designations, referring to the British Horticultural Colour Chart, and without chart designations referring to the conventional dictionary definition:

Parentage: Seedling.
- Seed parent.—"Heart's Desire" (Plant Patent No. 501).
- Pollen parent.—"Crimson Glory" (Plant Patent No. 105) × "Poinsettia."

Classification: Hybrid tea.

*Flower*

(Observations made in the morning in September at Van Nuys, California.)

Blooming habit:
- *Blooms.*—Profusely.
- *Recurrent.*—Continuous.
- *Other habit.*—Blooms freely in hot weather.

Bud:
- *Size.*—Medium.
- *Form.*—Long pointed. It's not affected by wet or hot weather.
- *Color.*—When sepals first divide—Turkey Red, Plate 721/2. When sepals unfurl—Turkey Red, Plate 721. When half-blown—inside of petals, Currant Red, Plate 821; reverse of petals, Crimson, Plate 22.

- *Sepals.*—Serrated. Back curl as soon as they break.
- *Calyx.*—Shape—funnel. Size—small. Aspect—smooth. Odor when rubbed—apple.
- *Peduncle.*—Length—long. Aspect—smooth; few very small needles. Color—Bronzy-green. Strength—stiff: slender.
- *Opening.*—Opens up well. Is not affected by cold, foggy weather.

Bloom:
- *Size.*—Medium.
- *Average size when fully expanded.*—Three to four inches.
- *Borne.*—Singly.
- *Stems.*—Medium length; normal.
- *Form.*—High center.
- *Permanence.*—Retains its form to end; outer petals curl back.
- *Petalage.*—Double. Number of petals under normal conditions, 30.
- *Color.*—Center of flower—Currant Red, Plate 821. Outer petals—Currant Red, plate 821. Base of petals (aiglet)—Aureolin, Plate 3/2. Inside of petals—Currant Red, Plate 821. Reverse of petals—Cardinal Red, Plate 822. General tonality from a distance—scarlet. Variations—none. Discolorations: General tonality at end of day—scarlet; second day—scarlet; third day—scarlet-crimson. Holds color for a long time.

Petals:
- *Texture.*—Thick. Is not affected by wet or hot weather.
- *Appearance.*—Inside and outside—satiny.
- *Form.*—Round. Arrangement—Imbricated. Petaloids in center—few. Persistence—drop off cleanly. Fragrance—very strong in half-open flower, not strong in open flower; nature—"Old Rose" perfume. Lasting quality—On plant, long; as cut-flower, very long.

Genital organs:
- *Stamens, anthers.*—Size—medium. Number—many; approximately 70. Color—yellow. Arrangement—regular around styles.
- *Stamens, filaments (threads).*—Length—long. Color—reddish brown.
- *Pollen.*—Golden yellow.
- *Styles.*—Bunched, uneven length, medium.
- *Stigmas.*—Red.
- *Ovaries.*—Some protruding from calyx.

Fruit: Variety is fertile with its own pollen.
- *Form.*—Funnel-shaped; seeds protruding.

*Aspect.*—Smooth.
*Color at maturity.*—Russet brown.
*Sepals.*—Permanent.

*Plant*

Form: Bush.
Growth: Vigorous; upright.
Foliage: Five to seven leaflets.
*Size.*—Medium.
*Color.*—New foliage — upper side: normal green-red edged; under side: light green. Old foliage—upper side: dark green; under side: light green.
*Shape.*—Lanceolate.
*Texture.* — Upper side and under side—smooth. Ribs and veins—ordinary.
*Edge.*—Serrated.
*Serration.*—Single; small.
*Leaf stem.* — Green. Under side—smooth.
*Stipules.*—Medium length; smooth.
*Disease resistance.*—Susceptible to mildew.

Wood:
*New Wood.*—Light green. Bark—smooth.
*Old Wood.*—Green. Bark—smooth.
Thorns:
*Thorns.*—Quantity—on main stalks from base and on laterals from stalk—few. Form — narrow base; medium length; hooked downward. Color when young—red. Position—irregular.
*Prickles and short needles.*—On main stalks and on laterals—none.

What is claimed is:

A new and distinct variety of hybrid tea rose plant characterized as to novelty by its profuse blooming habit, continuity of blooming, color of the flower and retention of form and color until blooms fall, substantially as shown and described.

LILLIAN ADELE MORRIS,
*Administratrix of the Estate of Theodore John Morris, Deceased.*